United States Patent [19]

Weyer et al.

[11] Patent Number: 5,157,127

[45] Date of Patent: Oct. 20, 1992

[54] PREPARATION OF N-SUBSTITUTED PYRROLIDONES

[76] Inventors: Hans-Juergen Weyer, 20 Neckarpromenade, 6800 Mannheim 1; Rolf Fischer, 98 Bergstrasse, 6900 Heidelberg; Wolfgang Harder, 16 Bergwaldstrasse, 6940 Weinheim, all of Fed. Rep. of Germany

[21] Appl. No.: 709,854

[22] Filed: Jun. 4, 1991

[30] Foreign Application Priority Data

Jun. 7, 1990 [DE] Fed. Rep. of Germany ....... 4018243

[51] Int. Cl.⁵ ............................................ C07D 207/26
[52] U.S. Cl. ..................................... 548/552; 548/554
[58] Field of Search ................................ 548/552, 554

[56] References Cited

U.S. PATENT DOCUMENTS

| | | | |
|---|---|---|---|
| 3,109,005 | 10/1963 | Lidov | 260/326.5 |
| 3,198,808 | 8/1965 | Himmele et al. | 548/554 |
| 3,884,936 | 5/1975 | Hollstein | 260/326.5 F X |

FOREIGN PATENT DOCUMENTS 40-9149   5/1965   Japan .................................. 548/554

*Primary Examiner*—David B. Springer
*Attorney, Agent, or Firm*—Keil & Weinkauf

[57] ABSTRACT

A process for the preparation of N-substituted pyrrolidones by the catalytic hydrogenation of maleic anhydride, maleic acid and/or fumaric acid in the presence of a primary amine and a solvent, at elevated temperature and pressure, wherein a catalyst is used which contains cobalt and at least one of the elements manganese, copper, phosphorus, molybdenum and/or sodium.

7 Claims, No Drawings

PREPARATION OF N-SUBSTITUTED PYRROLIDONES

The present invention relates to a process for the preparation of N-substituted pyrrolidones by the catalytic hydrogenation of maleic anhydride, maleic acid and/or fumaric acid in the presence of a primary amine and a solvent, at elevated temperature and pressure.

The abbreviations used below have the following meanings:
MAN: maleic anhydride
SAN: succinic anhydride
MA: maleic acid
FA: fumaric acid
SA: succinic acid
NMP: N-methyl pyrrolidone.

Numerous patent applications disclose methods of hydrogenating SAN/amine mixtures, N-substituted maleinimides or succinimides to N-substituted pyrrolidones in the presence of various special catalyst systems. All of these methods suffer from the drawback that the said starting materials must first be prepared, for example from MAN, in a separate reaction. Consequently, such methods are uneconomical and of no industrial significance for the preparation of N-substituted pyrrolidones.

On the other hand, there are only a few known processes which make it possible to prepare N-substituted pyrrolidones directly from MAN, MA and/or FA, as follows:

U.S. Pat. No. 3,109,005 describes a method of directly synthesizing N-methyl pyrrolidone (NMP) by hydrogenation of MAN/methylamine mixtures in contact with a Raney nickel catalyst at a temperature of 270° C., a pressure of 250 bar and in dioxane as solvent. With this method, reaction times of 10 hours give yields of NMP in the region of 70%.

DE-A 2,200,600 describes the hydrogenation of MAN/methylamine mixtures to NMP in contact with supported palladium catalysts. In this process, the most favorable conditions, i.e. a temperature of 275° C., a pressure of 120 bar and the use of water as solvent, give a yield of 44%. It is remarkable that almost identical reaction conditions used on the reaction system MAN/ammonia/water give yields of 2-pyrrolidone of up to 78%. This implies that NMP is obtainable by this method clearly more difficulty and in lower yields than 2-pyrrolidone.

Due to these moderate or unsatisfactory yields, the said processes cannot compete with the conventional methods of preparing NMP, i.e. by reacting λ-butyrolactone with methylamine, and have attained no industrial significance.

N-substituted pyrrolidones, particularly NMP, are manufactured in large quantities for use as solvents and extracting agents. MAN is a cheap basic chemical available in large quantities. It is thus an object of the present invention to provide an economical process for the direct synthesis of N-substituted pyrrolidones by catalytic hydrogenation of MAN/amine mixtures. A particular object of the invention is to provide a catalyst which makes it possible to prepare said pyrrolidones in good yields and which is characterized by a long useful life.

Accordingly, we have found a process for the preparation of N-substituted pyrrolidones by the catalytic hydrogenation of maleic anhydride, maleic acid and/or fumaric acid in the presence of a primary amine and a solvent, at elevated temperature and pressure, wherein a catalyst is used which contains cobalt and at least one of the elements manganese, copper, phosphorus, molybdenum and/or sodium.

The process of the invention basically relates to the hydrogenation of MAN(I)/amine mixtures to N-substituted pyrrolidones (II), formally represented by the following equation:

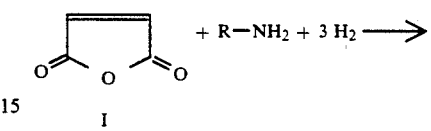

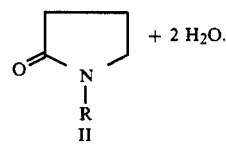

Examples of suitable primary amines $R-NH_2$ for use in this reaction are aliphatic amines having from 1 to 10, preferably from 1 to 4, carbon atoms, primary cycloaliphatic amines having from 5 to 8 carbon atoms or, alternatively, primary aromatic and araliphatic amines such as aniline or benzylamine. The following amines are examples of reactants which can be used with MAN: methylamine, propylamine, butylamine, hexylamine, decylamine, cyclopentylamine and cyclohexylamine. It is particularly preferred to carry out the reaction using methylamine.

The use of MA and/or FA as starting materials for the process of the invention is equivalent to the use of MAN. All of these starting materials may be introduced into the process of the invention in solid, liquid or gaseous form. We particularly prefer to use MAN. An advantageous procedure is to cause gaseous MAN, as normally produced industrially from the catalytic oxidation of butane, butene or aromatics, to be absorbed in a solvent and to pass the resulting solution without further treatment to the hydrogenation reaction.

According to the invention, the catalytic hydrogenation of MAN/amine mixtures is effected using a catalyst which contains cobalt and at least one of the elements manganese, copper, phosphorus, molybdenum and/or sodium. It is preferred to use catalysts which contain cobalt and at least two of the elements manganese, copper, phosphorus, molybdenum and/or sodium. Catalysts having particularly favorable properties when used in the process of the invention are those which contain cobalt and at least three of the elements manganese, copper, phosphorus, molybdenum and/or sodium. Catalysts of this kind are described in DE-A 2,321,101 and in DE-A 3,904,083.

Examples of advantageous catalysts for use in the process of the invention are those in which the active material contains at least 40% w/w of cobalt (calc. as Co), the other active ingredients comprising up to 10% and preferably from 3 to 7%, of manganese (calc. as Mn), up to 20% and preferably from 0.1 to 5%, of phosphoric acid and up to 1% and preferably from 0.01 to 0.5%, of sodium (calc. as Na), by weight. Of these catalysts, those are particularly preferred in which the active material contains, as said other active ingredients, up to 30% and preferably from 12 to 18%, of copper (calc. as Cu) and up to 5% and preferably from 1 to 4%, of molybdenum (calc. as Mo), by weight.

The catalysts to be used in the process of the present invention may be in the form of supported catalysts or, preferably, solid catalysts, i.e. unsupported catalysts. The type of support used is not normally critical and conventional support materials, such as silicon dioxide, aluminum dioxide, titanium dioxide, activated charcoal, silicates or zeolites, may be used. If necessary, the catalysts may be made with the aid of binders or shaping agents.

The catalysts are advantageously activated with hydrogen prior to use in the process of the invention. The active catalyst components are generally in the form of their oxides, following calcination, and the said treatment with hydrogen reduces them, usually to the corresponding metals. Further details on the manufacture of these catalysts can be found in DE-A 2,321,101 and DE-A 3,904,083.

The catalysts may be used in the process of the invention in the form of suspended particles, but it is preferred to use them in a fixed bed through which the components pass, either in a packed bubble column or, preferably, in a trickle-bed reactor.

The hydrogenation of the reactants MAN and primary amine, as proposed by the invention, is generally carried out in the presence of a solvent. Suitable solvents are virtually all those which are inert to the conditions of the hydrogenation, for example water, aliphatic and aromatic hydrocarbons or ethers such as diethyl ether, diisopropyl ether, methyl-t-butyl ether, dioxane or tetrahydrofuran, or mixtures of said solvents. In one advantageous embodiment, the solvent used comprises N-substituted pyrrolidones as produced in the hydrogenation of the invention. It is particularly preferred to use water as solvent, especially for the manufacture of NMP.

The order in which the reactants MAN, MA or FA and primary amine are added to the reaction mixture is not generally critical.

The molar ratio of MAN, MA or FA to the solvent is usually from 1:1 to 1:100 and is preferably from 1:5 to 1:50.

The molar ratio of MAN, MA or FA to the primary amine in the process of the invention is generally from 1:0.5 to 1:2, preferably from 1:0.8 to 1:1.5 and more preferably from 1:1 to 1:1.3.

The hydrogen is fed to the reaction in the stoichiometric amount or, preferably, in excess. The excess quantity of hydrogen used is not critical, as the excess, i.e. unconverted, hydrogen can be recycled to the reaction or, if desired, burnt off.

Since the hydrogenation reaction of MAN, MA or FA with primary amines and hydrogen to form N-substituted pyrrolidones proceeds via numerous intermediates, e.g. maleaminde, maleimide, SAN, SA, succinimide and succinamide, such intermediates can obviously themselves be used as starting materials for the hydrogenating reaction of the invention. That such a procedure is equivalent to the process of the invention is self-evident.

The reaction is generally carried out at a temperature of from 100° to 350° C., preferably from 150° to 300° C. and more preferably from 180° to 280° C. The pressure used is generally from 50 to 350 bar and preferably from 100 to 300 bar.

The reaction can be carried out batchwise, for example in stirred autoclaves. However, it is preferred to operate the process continuously, for example in tubular reactors or reactors incorporating a bundle of tubes, in which case the heat of hydrogenation can be removed by external or internal cooling. Another way of controlling the reaction temperature is to recycle part of the effluent and the excess hydrogen after these have been cooled in, say, a heat exchanger.

The hydrogenation reaction may be controlled in such a way that predetermined pressure and temperature ranges are maintained throughout the reaction. However, a positive effect on selectivity and catalyst useful life may be achieved, particularly when relatively large amounts of reactants are involved, by carrying out the reaction at different levels of pressure and temperature, for example by effecting partial hydrogenation in a first reactor at a temperature of from 100° to 220° C. and a pressure of from 50 to 200 bar and then transferring the effluent as it is to the next reactor in order to complete hydrogenation at, say, a temperature of from 220° to 300° C. and a pressure of from 200 to 350 bar.

The hydrogenated reaction mixtures thus obtained may in some cases contain not only the desired N-substituted pyrrolidones but also small amounts of by-products such as N-substituted succinimides, succinyl diamides, succinyl monoamides and N-substituted pyrrolidines. These mixtures can be worked up by extraction or, advantageously, by distillation. The separated, partially hydrogenated by-products may, since they are capable of being hydrogenated to N-substituted pyrrolidones, be recycled to the hydrogenation zone to complete their conversion.

The process of the invention enables N-substituted pyrrolidones to be directly produced from MAN, MA and/or FA and primary amines on an economical industrial scale. The yields obtained are more than 90%.

EXAMPLES

In the following Examples, the percentages are by weight.

EXAMPLE 1

The hydrogenation was carried out in a tubular reactor (length 200 mm, diameter 16 mm) packed with 38 g of catalyst as a fixed bed. The reactor was heated to the reaction temperature by oil contained in an external heating jacket. The gaseous and liquid starting materials pass downwardly through the reactor (trickle method). The hydrogenated effluent was cooled to room temperature, depressurized and passed to a gas-liquid separator to separate its gaseous and liquid components.

The catalyst used had the following composition:
63.4% of cobalt, calculated as CoO
18.1% of copper, calculated as CuO
6.8% of manganese, calculated as $Mn_3O_4$
3.1% of molybdenum, calculated as $MoO_3$
0.15% of sodium, calculated as $Na_2O$
3.3% of phosphoric acid ($H_3PO_4$).

The catalyst was used in the form of gravel (particle size 2.5 to 4 mm), which was activated with hydrogen before the commencement of the hydrogenation reaction.

At a total pressure of 200 bar and a temperature of 250° C., there were passed through the reactor, per kg of catalyst per hour, 0.15 kg of MAN, 0.07 kg of methylamine, 0.55 kg of water and 2,500 liters (STP) of hydrogen.

Analysis of the liquid effluent after a reaction time of 9 hours gave a yield of NMP of 91%, based on the weight of MAN used. There were also found about 2% of succinyl N-methylamide and about 1% of succinyl N-methylimide.

EXAMPLE 2

At a total pressure of 200 bar and a temperature of 210° C., there were passed through the reactor used in Example 1, per kg of catalyst per hour, 0.1 kg of MAN, 0.15 kg of cyclohexylamine, 0.29 kg of dioxane, 0.29 kg of water and 2,000 liters (STP) of hydrogen. The yield of N-cyclohexyl pyrrolidone, as determined by gas chromatography, was 51%, based on the weight of MAN used.

We claim:

1. A process for the preparation of N-substituted pyrrolidones which comprises:

catalytically hydrogenating maleic anhydride, maleic acid and/or fumaric acid in the presence of a primary aliphatic amine having from 1 to 10 carbons, a primary cycloaliphatic amine having from 5 to 8 carbons or a primary aromatic or araliphatic amine, and in the presence of a solvent, at a temperature of from 100° to 350° C. and under a pressure of from 50 to 350 bar, said catalyst containing at least 40% w/w of cobalt (calc. as Co), 3 to 10 w/w of manganese (calc. as Mn), 0.1 to 20% w/w of phosphoric acid, 0.01 to 1% of sodium (calc. as Na), 12 to 30% w/w of copper (calc. as Cu) and 1 to 5% w/w of molybdenum (calc. as Mo).

2. A process as defined in claim 1, wherein maleic anhydride is catalytically hydrogenated.

3. A process as defined in claim 2, wherein the molar ratio of maleic anhydride to amine is from 1:0.5 to 1:2.

4. A process as defined in claim 2, wherein the molar ratio of maleic anhydride to solvent is from 1:1 to 1:100.

5. A process as defined in claim 1, wherein the solvent used is water.

6. A process as claimed in claim 1, wherein the hydrogenation is carried out at two different temperature and pressure levels, partial hydrogenation being first carried out at a temperature of from 100° to 220° C. and under a pressure of from 50 to 200 bar, after which hydrogenation is completed at a temperature of from 220° to 350° C. and under a pressure of from 200 to 350 bar.

7. A process as defined in claim 1, wherein the amine used is methylamine.

* * * * *

UNITED STATES PATENT AND TRADEMARK OFFICE
CERTIFICATE OF CORRECTION

PATENT NO. : 5,157,127
DATED : October 20, 1992
INVENTOR(S) : WEYER et al.

It is certified that error appears in the above-identified patent and that said Letters Patent is hereby corrected as shown below:

Col. 6, line 16, "claimed" should read --defined--

Signed and Sealed this

Eighteenth Day of January, 1994

Attest:

BRUCE LEHMAN

Attesting Officer

Commissioner of Patents and Trademarks